(12) United States Patent
Tanabe et al.

(10) Patent No.: US 11,566,232 B2
(45) Date of Patent: Jan. 31, 2023

(54) CELL CULTURE SUBSTRATE, CELL CULTURE VESSEL, AND METHOD FOR CELL CULTURE

(71) Applicants: HITACHI, LTD., Tokyo (JP); The University of Tokyo, Tokyo (JP)

(72) Inventors: Maiko Tanabe, Tokyo (JP); Shizu Takeda, Tokyo (JP); Masahiro Okanojo, Tokyo (JP); Hiroko Hanzawa, Tokyo (JP); Masao Washizu, Tokyo (JP); Kennedy Omondi Okeyo, Tokyo (JP)

(73) Assignees: HITACHI, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 579 days.

(21) Appl. No.: 16/122,912

(22) Filed: Sep. 6, 2018

(65) Prior Publication Data
US 2019/0085299 A1 Mar. 21, 2019

(30) Foreign Application Priority Data
Sep. 15, 2017 (JP) .............................. JP2017-177814

(51) Int. Cl.
C12N 5/074 (2010.01)
C12N 5/00 (2006.01)
C12M 1/12 (2006.01)
C12M 1/00 (2006.01)

(52) U.S. Cl.
CPC ........... *C12N 5/0696* (2013.01); *C12M 23/20* (2013.01); *C12M 25/02* (2013.01); *C12M 25/14* (2013.01); *C12N 5/0068* (2013.01); *C12N 2533/00* (2013.01); *C12N 2533/30* (2013.01); *C12N 2533/54* (2013.01); *C12N 2535/00* (2013.01); *C12N 2535/10* (2013.01)

(58) Field of Classification Search
CPC ............... C12N 5/0696; C12N 5/0068; C12N 2533/30; C12N 2533/00; C12N 2535/00
See application file for complete search history.

(56) References Cited

FOREIGN PATENT DOCUMENTS

| JP | 2013-503014 A | 1/2013 |
| WO | 2015/005349 A1 | 1/2015 |
| WO | 2017/051650 A1 | 3/2017 |

OTHER PUBLICATIONS

Yoo et al., Simple and novel three dimensional neuronal cell culture using a micro mesh scaffold. Experimental Neurobiology, vol. 20, No. 2 (Jun. 30, 2011) pp. 110-115. (Year: 2011).*

Sun et al., Development of a mini 3D cell culture system using well defined nickel grids for the investigation of cell scaffold interactions. Journal of Materials Science: Materials in Medicine, vol. 20 (2009) pp. 1483-1493. (Year: 2009).*

Okeyo et al., Cell adhesion minimization by a novel mesh culture method mechanically directs trophoblast differentiation and self-assembly organization of human pluripotent stem cells. Tissue Engineering Part C: Methods, vol. 21, No. 10 (Jun. 3, 2015) pp. 1105-1115. (Year: 2015).*

Nguyen, Q.. "Charaterization of biocompatible parylene-C coating for BioMEMS applications" (2011), pp. 1-58, Retrieved from the Internet <URL: https://digitalcommons.lsu.edu/cgi/viewcontent.cgi?article=2477&context=gradschool_theses> (Year: 2011).*

Extended European Search Report received in corresponding European Application No. 18193513.1 dated Jan. 17, 2019.

Okeyo, K. O. et al., "Cell Adhesion Minimization by a Novel Mesh Culture Method Mechanically Directs Trophoblast Differentiation and Self-Assembly Organization of Human Pluripotent Stem Cells", Tissue Engineering. Part C, Methods Dec. 2008, Oct. 1, 2015, pp. 1105-1115, vol. 21, No. 10.

Epstein, J. et al., "Stainless Steel Mesh Supports High Density Cell Growth And Production of Recombinant Mullerian Inhibiting Substances", In Vitro Cellular & Developmental Biology, Feb. 1, 1989, pp. 213-216, vol. 25.

Sun, T. et al., "Development of a Mini 3D Cell Culture System Using Well Defined Nickel Grids for the Investigation of Cell Scaffold Interactions", Journal of Materials Science: Materials in Medicine, Jul. 1, 2009, pp. 1483-1493, vol. 20, No. 7.

Yoo, S. J. et al., "Simple and Novel Three Dimensional Neuronal Cell Culture Using a Micro Mesh Scaffold", Experimental Neurobiology, Jan. 1, 2011, pp. 110-115, vol. 20, No. 2.

Kuo, S. M. et al., "Plasma-Modified Nylon Meshes as Supports for Cell Culturing", Art. Cells, Blood Subs., and Immon. Biotech., Jan. 1, 1997, pp. 551-561, vol. 25, No. 6.

Anonymous, "Data Sheet Product Selection Guide Cell Culture Solutions", Jan. 1, 2008, pp. 1-16, URL: http://static.fishersci.com/cmsassets/downloads/segment/Scientific/pdf/Millipore/millicell_cellcult_sol.pdf.

Cieslik, M. et al., "Parylene Coatings on Stainless Steel 316L Surface for Medical Applications—Mechanical and Protective Properties", Materials Science and Engineering C, Elsevier Science S.A, CH, Sep. 14, 2011, pp. 31-35, vol. 32, No. 1.

Okeyo, K. O. et al., "Self-Organization of Human iPS Cells into Trophectoderm Mimicking Cysts Induced by Adhesion Restriction Using Microstructured Mesh Scaffolds", Development Growth and Differentiation, Apr. 1, 2008, pp. 183-194, vol. 60, No. 3.

Hori, T. et al., "A Three-Dimensional Cell Culture Method with a Micromesh Sheet and Its Application to Hepatic Cells", Tissue Engineering: Part C, Methods Dec. 2008, Dec. 1, 2018, pp. 730-739, vol. 24, No. 12.

Communication Pursuant to Article 94(3) EPC received in corresponding European Application No. 18 193 513.1 dated Feb. 10, 2020.

Chang, T. Y. et al., "Cell and Protein Compatibility of Parylene-C Surfaces", Langmuir, Nov. 1, 2007, pp. 11718-11725, vol. 23, No. 23.

(Continued)

*Primary Examiner* — Kara D Johnson
(74) *Attorney, Agent, or Firm* — Mattingly & Malur, PC (57) ABSTRACT

The purpose of the invention is to provide novel cell culture substrates, cell culture vessels, and methods for cell culture. A cell culture substrate having a planar mesh structure, the substrate being coated with a polymer, is provided. Cells are cultured in a cell culture vessel having this substrate.

10 Claims, 11 Drawing Sheets

(56) References Cited

OTHER PUBLICATIONS

Lu, B. et al., "Mesh-Supported Submicron Parylene-C Membranes for Culturing Retinal Pigment Epithelial Cells", Biomedical Microdevices, Mar. 4, 2012, pp. 659-667, vol. 14, Np. 4.

Communication Pursuant to Article 94(3) EPC received in corresponding European Application No. 18 193 513.1 dated Sep. 28, 2020.

Nguyen, Q., "Lousiana State University Characterization of Biocompatible Parylene-C Coating for BioMEMS Applications", LSU Digital Commons, Jan. 1, 2011, pp. 1-58, URL: https://digitalcommons.lsu.edu/cgi/viewcontent.cgi?article=24 77 &context=gradschool_theses.

Notification dated Aug. 13, 2020, received in corresponding Japanese Patent Application No. 2017-177814.

* cited by examiner

Fig. 6(A) Mesh made of metal

Fig. 6(B) Mesh made of photocurable resin

Mesh with equilateral triangular openings

Fig. 9(B)

Mesh with circular openings

Mesh with diamond-shaped openings

Fig. 10(A)

Mesh with circular openings

CELL CULTURE SUBSTRATE, CELL CULTURE VESSEL, AND METHOD FOR CELL CULTURE

CROSS REFERENCE TO RELATED APPLICATIONS

This application claims priority to Japanese Patent Application No. 2017-177814 filed on Sep. 15, 2017, which is hereby incorporated by reference in its entirety.

TECHNICAL FIELD

The present invention relates to cell culture substrates, cell culture vessels, and methods for cell culture.

BACKGROUND ART

Induced pluripotent stem (iPS) cells are adherent cells that are cultured by allowing them to attach to a vessel or a cell culture substrate and are typically cultured by seeding and growing them on the bottom surface of a vessel or a substrate. In these cases, when cells are grown to confluent, they stop proliferation due to their contact inhibition, resulting in cell death, differentiation, or transformation. Accordingly, the cells need to be passaged when the cells reach about 80% confluence.

In current automatic cell culture devices, there is a risk of contamination with microorganisms during the passage because it is performed manually. Moreover, the passage operation itself has an adverse effect on the cells and pluripotency decreases through repeated passages to make it difficult to obtain high quality cells. Thus, methods have been developed in which cells can be cultured for a long time by culturing them on a micromesh (WO2015/005349).

An object of the present invention is to provide novel cell culture substrates, cell culture vessels, and methods for cell culture.

SUMMARY OF THE INVENTION

An aspect of the present invention is a substrate for culturing a cell, the substrate having a planar mesh structure and being coated with a polymer. The substrate may contain a metal and the metal may be nickel. Further, the planar mesh structure may be made of wire-like substrates, each wire-like substrate having a maximum diameter of 10 μm or smaller, and the planar mesh structure may include openings each having a maximum width of 30 μm or larger. Each opening of the mesh may have an area that is equal to or larger than an area of a cell to be cultured or may be 100 μm$^2$ or larger. The cell may be a stem cell such as a pluripotent stem cell. The polymer may be a p-xylene polymer. The substrate may be coated with the polymer, the polymer being coated with a scaffold material for the cell.

Another aspect of the present invention is a cell culture vessel including a holding mechanism for holding the substrate according to any one of the substrates above in a state of being suspended in a culture medium. The vessel may include a plurality of holding mechanisms.

A still another aspect of the present invention is a method for cell culture including the steps of seeding a cell on the substrate according to any one of the substrates above; and culturing the cell with the substrate held in a state of being suspended in a culture medium. The cell may be cultured with a plurality of substrates stacked in a single cell culture vessel.

INDUSTRIAL APPLICABILITY OF THE INVENTION

The present invention made it possible to provide novel cell culture substrates, cell culture vessels, and methods for cell culture.

DETAILED DESCRIPTION OF THE INVENTION

Hereinafter, embodiments of the present invention are described in detail with reference to the drawing. The objects, features, advantages, and ideas of the present invention are apparent to those skilled in the art from the description of this specification. Those skilled in the art can easily reproduce the present invention from the description herein. The embodiments and specific examples described below represent preferable aspects of the present invention, which are given for the purpose of illustration or explanation. The present invention is not limited thereto. It is obvious to those skilled in the art that various modifications may be made according to the description of the present specification within the spirit and scope of the present invention disclosed herein.

1. Planar Mesh

The cell culture substrates according to embodiments of the present invention are described. The substrates have a planar mesh structure. When a cell culture substrate is placed in a culture medium, cells adhere to the substrate and spontaneously spread in openings of the planar mesh 1 each of which has an area larger than an area occupied by a cell, instead of adhering to and proliferating on a scaffold larger in area than a cell or a scaffold with gaps smaller in area than a cell like conventional cell culture substrates. The cells then proliferate on the substrate and a plurality of the cells fills each opening 2. Further, the substrate may be suspended in a culture medium in a culture vessel. Furthermore, it is preferable that the cell culture substrate according to the present invention is made of a material with a high strength in order to enlarge the area for culturing. Hereinafter, specific embodiments are described in detail with reference to the drawings.

Figure 1A:
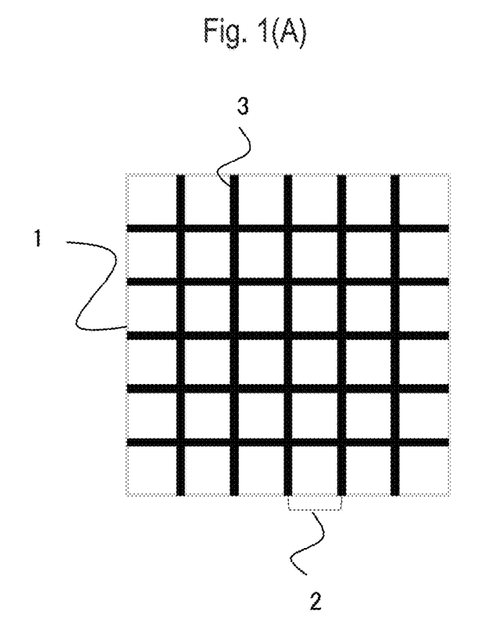
FIGS. 1(A) and 1(B) are top views of a cell culture substrate according an embodiment of the present invention.
Figure 1B:
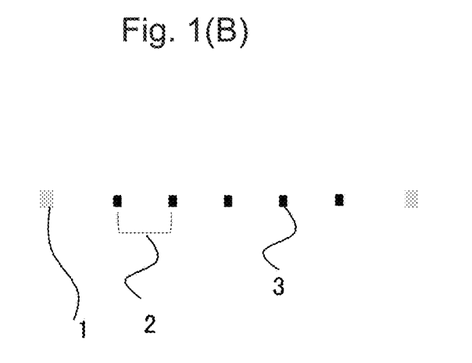

A diagrammatic representation of an example of a planar mesh 1 composed of a cell culture substrate is shown in FIGS. 1(A) and 1(B).

Any material can be used for producing the cell culture substrate, but it is preferable that the material is or includes a strong metal with no cytotoxicity such as pure nickel, titanium, platinum, gold, tungsten, rhenium, palladium, rhodium, ruthenium, and alloys (e.g., stainless steel, titanium/nickel, nitinol, cobalt-chromium, nonferrous alloys, and platinum iridium alloys). Further, if a sufficient strength is obtained, the material may include, for example, a photocurable resin, a biocompatible material, or a biodegradable material. Examples of photocurable resins include, but not limited to, acrylate compounds, methacrylate compounds, epoxy compounds, isocyanate compounds, thiol compounds, silicone compounds; specifically, urethane acrylate, polyester acrylate, epoxy acrylate, poly(methyl acrylate), poly(methyl methacrylate), ethoxylated bisphenol A acrylate, aliphatic urethane acrylate, polyester acrylate, polyethylene terephthalate, polystyrene, polycarbonate, acrylic modified alicyclic epoxide, epoxides which are ethers with a bifunctional alcohol, acrylic silicone, and acrylic dimethyl siloxane. In respect to suitable applicability of the substrate to regenerative medicine such as direct transplantation to a living body, it is preferable that the material of the substrate is made of or includes a biocompatible or biodegradable material. Examples of biocompatible materials include, but not limited to, silicone, polyether block amide (PEBAX), polyurethane, silicone-polyurethane copolymers, ceramics, collagen, hydroxyapatite, nylon, polyethylene terephthalate, ultrahigh molecular weight polyethylene such as Gore-Tex™, polyvinyl chloride, and other materials derived from living bodies. Examples of biodegradable materials include, but not limited to, polylactide (PLA), polyglycolide (PGA), polycaprolactone (PCL), and copolymers thereof; PHB-PHV poly(alkanoates); polyesters; and natural polymers such as starch, cellulose, chitosan, and derivatives thereof.

The cell culture substrates can be suitably made by a person skilled in the art using the material(s) mentioned above with a known method or a similar method depending on, for example, the structure and use thereof. It is, however, preferable that the substrate is the planar mesh 1 composed of wire-like substrates. For example, the mesh can be made by, for example, electroforming for pure nickel or titanium or by photolithography for a photocurable resin. If the material of a substrate is cytotoxic or is not a biocompatible material, the surface of the wire-like substrate may be treated with, for example, a biocompatible material.

The wire-like substrate may have any diameter and a person skilled in the art can appropriately determine the diameter depending on the material and the size of cells to be cultured. For conventional cell culture substrates, a structure having a width almost equal to or larger than the maximum diameter of the individual cells was used so that the cells could adhere thereto, whereas the diameter of the wire-like substrate according to the present invention may be smaller than the maximum diameter of the cells. For example, the diameter may be one half or less, one third or less, one fourth or less, one fifth or less, or less of the maximum diameter of the cells. Specifically, the diameter of the wire-like substrate may be 1 to 10 µm, or 1 µm or less. Since cells adhere to the cell culture substrates when they are initially seeded on the planar mesh 1, the number of cells to adhere can be controlled by adjusting the diameter of the wire-like substrate. As used herein, the "maximum diameter of a cell" means the length of the longest straight line connecting two points on the contour of the cell.

Next, using wire-like substrates, the planar mesh 1, that is, a planar structure in which the openings 2 are regularly or irregularly arranged is prepared. The shape of openings 2 is typically a regular polygon such as an equilateral triangle, a square or a regular hexagon, but it may be another polygon as well as a circle or an ellipse. When the opening has a shape of a regular polygon, each side may have any length such as about 30 to 400 µm. Further, all of the openings 2 need not have the same shape. The substrate may be a planar structure with sets of different openings regularly or irregularly arranged. The shapes of the openings 2 may be randomly varied, or all of the openings 2 may have different shapes.

It is preferable that the openings 2 have sizes equal to or larger than the sizes of single cells to be cultured, that is, the sizes to allow the cells to pass through the openings 2. In this case, the openings 2 may have sizes that allow the cells to pass through without contacting the openings 2; to pass through in contact with the wire-like substrate but with no deformation; or to pass through with deformation in contact with the openings 2.

An example in which the openings 2 have sizes equal to or larger than the sizes of the cells to be cultured is a case where the areas of openings 2 of the mesh structure are larger than the maximum area of the cells before being seeded. As used herein, the "maximum area of a cell" refers to a cross-sectional area of the cells when they are cut to have the maximum cross-sectional area. The "maximum area of a cell before being seeded" means the maximum area of the cell in a state before being seeded, that is, before the cell adheres to the cell culture substrate and spreads. Since cells usually have a shape close to a sphere before adhesion, they can easily pass through the openings 2 of the mesh structure if the areas of openings 2 of the mesh structure are larger than the maximum area of single cells before being seeded. As another example, the minimum diameter of the openings 2 may be larger than the maximum diameter of the cells to be cultured before being seeded. For example, the minimum diameter of the openings 2 may be 2 times, 3 times, 4 times, 5 times, 7 times, 10 times, 100 times, or 1000 times the maximum diameter of the cells to be cultured. The minimum diameter of the openings 2 can appropriately be measured by a person skilled in the art, but refers to, for example, the length of the shortest straight line connecting two points on the side through the center of gravity of the shape of the openings 2 (e.g., the center for a regular polygon). In the case where the mesh has the openings 2 of two or more different shapes, the minimum diameters of one or more but not all of the openings 2 may be larger than the maximum diameter of the cells to be cultured before being seeded, or the minimum diameters of all openings may be larger than the maximum diameter of the cells to be cultured before being seeded.

Although the areas of the openings 2 may have any value, the areas are preferably 50 $\mu m^2$, more preferably 100 $\mu m^2$, and still more preferably 200 $\mu m^2$ or larger.

Further, the periphery of the cell culture substrate may be reinforced, which facilitates culturing of the cells as well as manipulation such as removal and shaping thereof. Examples of methods of reinforcing the cell culture substrate include methods of sticking a Kapton tape around it and sandwiching it with PDMS or the like.

With the minimum diameter of the openings 2 larger than the maximum diameter of the cell, when the cell culture substrate is placed horizontally and cells are seeded from above, some cells settle onto the substrate and others fall down without contacting the substrate. The openings 2 are not filled with the cells settled onto the substrate at the beginning, but as cells spread spontaneously toward the center of the opening, the openings 2 are gradually filled with the cells.

2. Pretreatment of the Cell Culture Substrate

The cell culture substrate may be coated with a material that serves as a scaffold for adherent cells as a pretreatment for use in cell culture in order to allow the cells to stay on the substrate and facilitate spreading and proliferation. Examples of materials that serve as this scaffold include, but not limited to, extracellular matrix proteins such as collagen, fibronectin, and laminin, and positively charged substances such as poly L lysine. Coating can be applied by, in the case of collagen for example, immersing the substrate in a solution of approximately 0.1% collagen, followed by incubating. For fibronectin, a solution at a concentration of approximately 10 $\mu g/ml$, and for Matrigel, a 1% solution can be used. The concentrations, treatment temperature and treatment time can appropriately be adjusted by those skilled in the art.

Further, it becomes possible to control the properties of cultured cells by coating the cell culture substrate with a monomer or polymer or a mixture thereof (hereinafter these three are collectively referred to as "monomer/polymer") before coating the substrate with the scaffold material for adherent cells. For example, when culturing pluripotent stem cells, it becomes possible to culture them while maintaining their properties as undifferentiated pluripotent stem cells by coating it with a monomer/polymer. Any monomer/polymer can be used as long as it has no cytotoxicity and is biocompatible. Examples include acrylic resins (e.g., methyl acrylate, methyl methacrylate, 2-hydroxyethyl methacrylate, 2-hydroxyethyl acrylate, acrylic acid, methacrylic acid, glyceryl acrylate, glyceryl, glyceryl methacrylate, methacrylamide, and acrylamide), vinyl (e.g., ethylene, propylene, chloroethylene, vinyl acetate, vinyl pyrrolidone, and vinylidene fluoride), nylon (e.g., polycaprolactam, polylauryllactam, polyhexamethylene biguanide, adipamide, and polyhexamethylene dodecanediamine), polyurethane, polycarbonate, polyamide, polysulfone, polyethylene terephthalate, dimethyl polysiloxane, polyether ketone, perfluoroalkoxy fluorine resin (e.g., Teflon (registered trademark), Neoflon (registered trademark), and polychlorotrifluoroethylene), ethylene propylene fluoride polymers (e.g., tetrafluoroethylene and hexafluoropropene), and expanded polytetrafluoroethylene. In particular, a p-xylene resin is preferable, poly-p-xylene is more preferable, and parylene is still more preferable.

The coating method is not particularly limited and coating methods that are most appropriate for each monomer/polymer may be used, such as vapor deposition. It is only necessary for the thickness of the coating that the diameter of the wire-like substrate does not exceed the maximum cross-sectional length of the cells. For example, poly-p-xylene can be coated at a thickness of 100 to 500 nm.

3. Cell Culture Vessel

An embodiment of the present invention is a cell culture vessel 5 for culturing cells 7 including the aforementioned cell culture substrate 4.

Figure 2A:
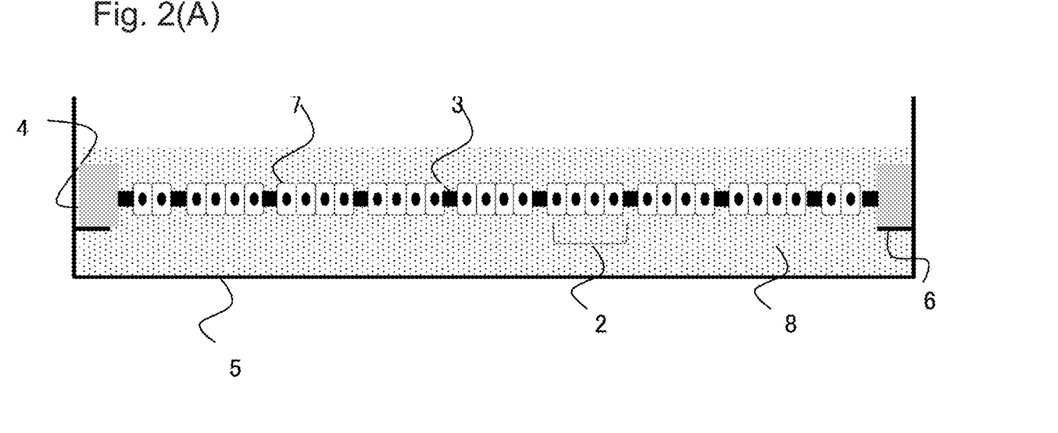
FIGS. 2(A) and 2(B) are cross-sectional views of a cell culture vessel according to an embodiment of the present invention.
Figure 2B:
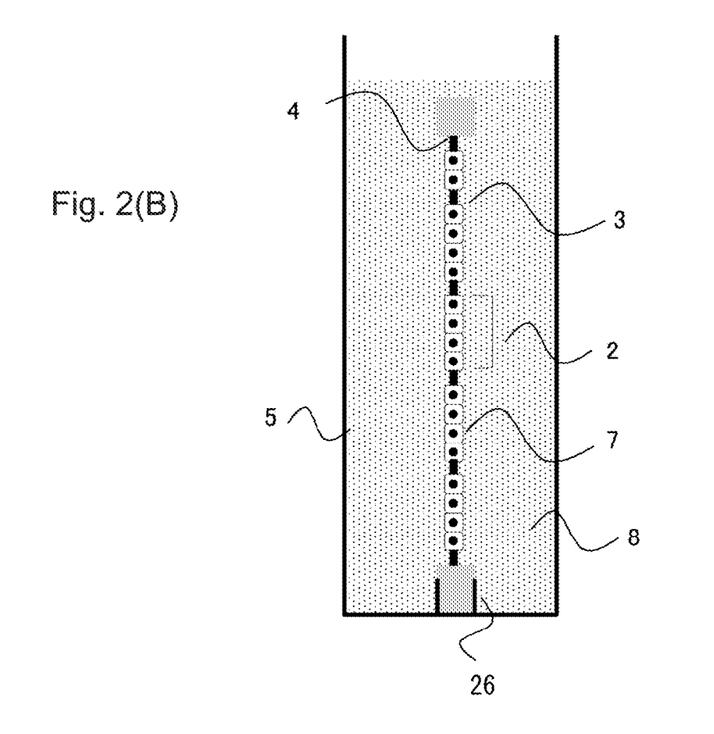

The cell culture vessel 5 may be provided with a holding mechanism 6 for holding the cell culture substrate 4 in a state of being suspended in a culture medium. The expression "in a state of being suspended in a culture medium" refers to a state where both surfaces of the cell culture substrate 4 are not in contact with the inner wall and the bottom surface of the cell culture vessel 5, and both surfaces can sufficiently contact the culture medium. For example, as shown in FIGS. 2(A) and 2(B), the cell culture substrate 4 may be placed horizontally (FIG. 2A) or vertically in the cell culture vessel 5 (FIG. 2B). In the present specification, "a holding mechanism for holding the substrate in a state of being suspended in a culture medium" may be any means as long as the cell culture substrate 4 can be stably held while being suspended in the culture medium. For example, the holding mechanism 6 may be a groove 26 provided in the inner wall (FIG. 2A) of the cell culture vessel 5. As shown in FIG. 2B, when holding the cell culture substrate 4 vertically, the groove 26 is provided in the cell culture vessel. In general, stem cells with a high proliferative capacity often stack and accumulate to form spheres during culture and cells may die from the inside of the spheres because nutrients from the culture medium do not reach the cells at the center of the spheres. In contrast, when cells are cultured with the cell culture substrate placed vertically, excess cells are detached from the cell culture substrate 4 and the formation of colonies can be suppressed.

Figure 3A:
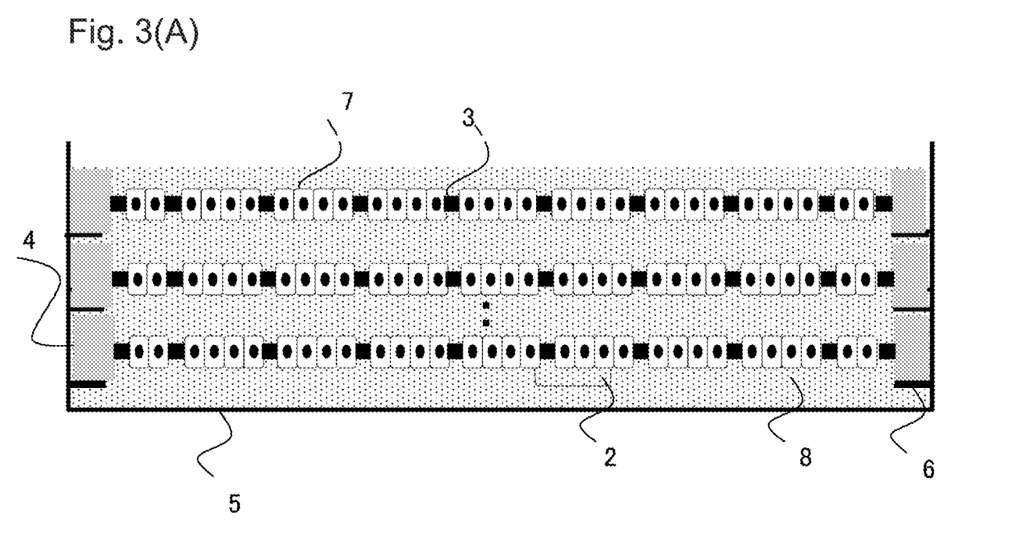
FIGS. 3(A) and 3(B) are cross-sectional views of a cell culture vessel according to an embodiment of the present invention, in which cell culture substrates are stacked.
Figure 3B:
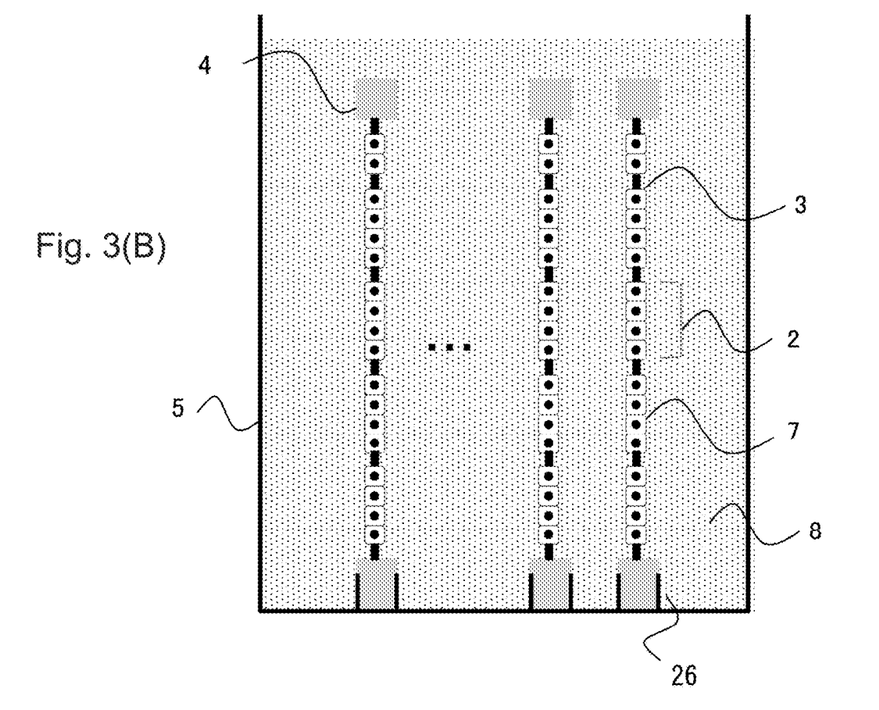

The cell culture vessel 5 may be configured so that a plurality of cell culture substrates 4 can be mounted. For example, as shown in FIGS. 3(A) and 3(B), by forming a plurality of holding mechanisms 6 for holding the cell culture substrate in a state of being suspended in a culture medium and mounting a plurality of cell culture substrates 4 so that they are perpendicular to the bottom surface or the wall, it is possible to install the plurality of cell culture substrates 4 in parallel. With these configurations, a large quantity of cells can be cultured with a small space.

4. Cell Culture Device

Cell culture devices according to an embodiment of the present invention are devices for culturing cells using the cell culture vessel mentioned above. The cell culture devices are for allowing automatic or partially manual cell culturing, that is, the steps of seeding cells on a cell culture substrate and culturing the cells. The cell culture devices include a cell culture vessel for holding the cell culture substrate with desired cultured cells adhered, a culture medium tank for supplying a medium to the cell culture vessel, a waste liquid tank for storing the medium discharged from the cell culture vessel, and a temperature/carbon dioxide concentration regulation mechanism for regulating the temperature and partial pressure of carbon dioxide in the cell culture devices.

Figure 4:
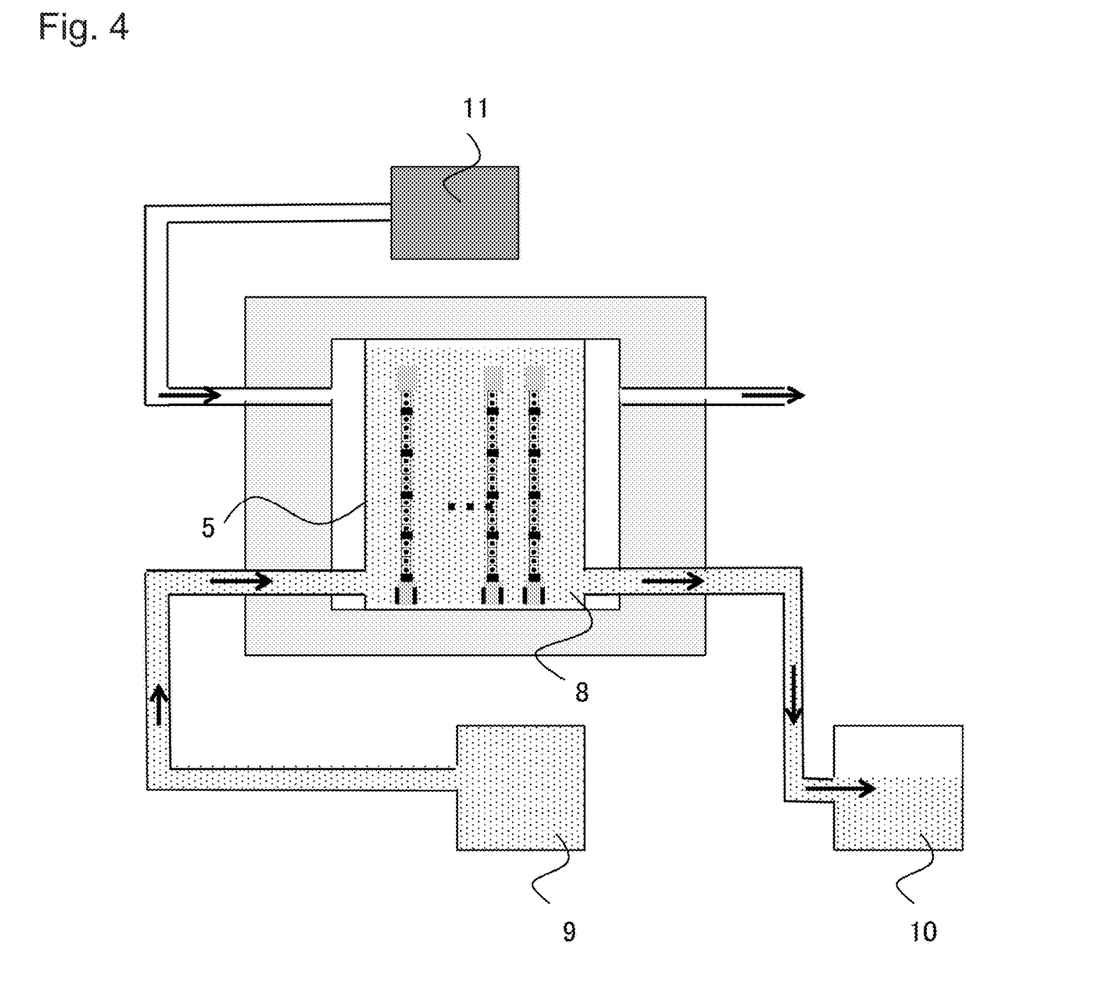
FIG. 4 is a cross-sectional view of a cell culture device according an embodiment of the present invention.

A method of culturing cells in one embodiment of the cell culture device shown in FIG. 4 is described below.

First, the cell culture vessel 5 having a cell culture substrate to which target cells are attached is prepared either by seeding the cells on the substrate after placing the substrate in the cell culture vessel 5 or placing the substrate in the cell culture vessel after seeding the cells on the substrate. Next, a valve to a waste liquid tank 10 is closed and a certain volume of medium is supplied from a culture medium tank 9. A valve from the culture medium tank 9 is closed and cells are incubated for a certain period of time. Meanwhile, a temperature/carbon dioxide concentration regulation mechanism 11 keeps the temperature and the carbon dioxide partial pressure in the cell culture device constant. Thereafter, the valve to the waste liquid tank 10 is opened, and the medium is discharged to the waste liquid tank 10. Then, the valve to the waste liquid tank 10 is closed again, and a certain volume of medium is supplied from the culture medium tank 9. The valve from the culture medium tank 9 is closed and cells are incubated for a certain period of time. The opening and closing of the valves of the culture medium tank 9 and the waste liquid tank 10 can appropriately be adjusted. For example, when supplying the medium from the culture medium tank 9, the valve of the waste liquid tank 10 may be opened to replace and circulate the medium at a low flow rate. By repeating this process, cells are cultured. It is preferable that the cell culture devices have a control device for automatically performing all processes after the preparation of the cell culture vessel 5.

5. Method for Cell Culture

The method for cell culture, which is one embodiment of the present invention, includes the steps of seeding cells on the cell culture substrate mentioned above and culturing the cells while holding the substrate in a state of being suspended in a culture medium.

Any cells may be used herein but cells can preferably adherent culturable cells, more preferably stem cells, and still more preferably pluripotent stem cells. Pluripotent stem cells are those which can be cultured in vitro and can differentiate into almost all cells constituting a living body. Specifically, examples include ES cells, pluripotent stem cells derived from fetal primordial germ cells (EG cells: Proc. Natl. Acad. Sci. USA, A. 1998, 95: 13726-31), testicular-derived pluripotent stem cells (GS cells: Nature. 2008, 456: 344-9), somatic cell derived induced pluripotent stem cells (iPS cells), human pluripotent somatic stem cells (e.g., neural stem cells), but iPS cells and ES cells are preferable, and iPS cells are more preferable.

It is preferable to sterilize the cell culture vessel and cell culture substrate prior to the step of seeding the cells on the substrate. A culture medium can appropriately be prepared by a person skilled in the art depending on the kind of cells.

To seed cells on the cell culture substrate, a solution in which the cells are suspended is added onto the substrate to allow the cells to adhere to the substrate. This step can appropriately be performed by a known method or its modified method. For example, cells may be suspended in a culture medium and the medium may be dropped on the substrate with a tool such as a pipette. The cell suspension necessary for this step can be prepared with a medium recommended for each kind of cells by adjusting the number of cells appropriately in consideration of the culture area. After seeding the cells on the cell culture substrate, the substrate is placed in the cell culture vessel in a state of being suspended in the culture medium. By placing the substrate in a state of being suspended in the culture medium, all cells can take necessary nutrients from the culture medium and discharge unnecessary substances into the culture medium; therefore, culture conditions suitable for the cells can be maintained. Subsequently, the cell culture substrate is placed in an environment suitable for the culture, and the medium is replaced periodically. For the culture medium and the culture environment (e.g., the temperature and carbon dioxide concentration) used for the culture and the timing of replacing the medium, known conditions recommended for the cells to be used can be adapted.

With this method for cell culture, dead cells and damaged cells naturally fall out of the cell culture substrate so that there is no need to passage the cells, and it is possible to culture cells for a long period of time in the cell culture vessel by replacing or circulating the culture medium as necessary while maintaining the substrate in the cell culture vessel.

EXAMPLES

Hereinafter, the present invention is described specifically based on Examples, but the present invention is not limited thereto.

Example 1

In this Example, shown is an example in which a planar mesh was produced using a metal or photocurable resin and iPS cells were cultured on the mesh to differentiate.

First, a mesh 12 with diamond-shaped openings 2 each having a minor axis of 200 μm and wires 3 of 5 μm in diameter was produced.

A mesh with diamond-shaped openings of a photocurable resin was produced using SU-8 and photolithography as follows. First, a square mesh pattern was drawn on a photomask blank by electron beam drawing using a VDEC's electron beam drawing machine of the University of Tokyo. Subsequently, gelatin serving as a sacrificial layer was applied by spin coating onto the surface of a 4-inch silicon wafer. Then, SU-8 was spin-coated on the gelatin to a thickness of 2 μm. Thereafter, the wafer was subjected to soft baking stepwise by heating it at 65° C. for 1 minute and 95° C. for 2 minutes, then exposed and developed. Thereafter, a Kapton tape having a thickness of 100 μm was attached to the periphery of the mesh pattern for reinforcement, and then the wafer was immersed in hot water at 80° C. to dissolve the gelatin. The SU-8 thin film formed on the wafer was recovered to obtain a cell culture substrate.

A metal mesh with diamond-shaped openings was made by electroforming using pure nickel. The nickel mesh was also reinforced along the periphery thereof with a Kapton tape 13 having a thickness of 100 μm to facilitate handling.

The cell culture substrate 12 thus produced was irradiated with a UV lamp for 24 hours or more to be sterilized. The sterilized cell culture substrate 12 was placed in the cell culture vessel 5 using the configuration shown in FIG. 2A.

Figure 6A:
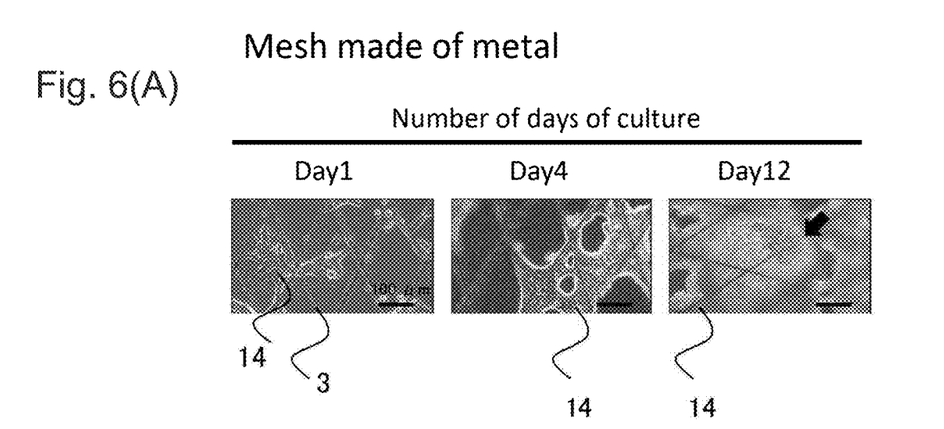
FIGS. 6(A) and 6(B) show bright-field microscopic images showing results of observation of cell culture on a mesh with diamond-shaped openings made of a metal; and a mesh with diamond-shaped openings made of a photocurable resin, respectively, according to Example 1 of the present invention.
Figure 6B:
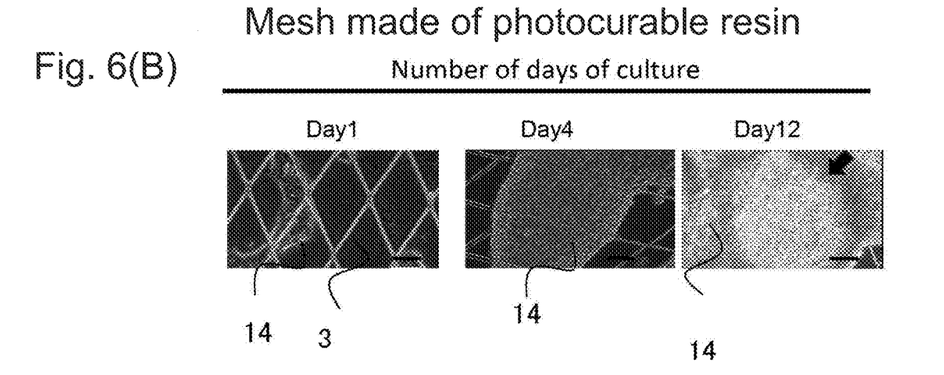

Next, Matrigel (CORNING) adjusted to a concentration of 1 mg/mL was added over the mesh and treated at 4° C. for 10 days. Subsequently, the Matrigel was removed and the Matrigel left in places other than the mesh was washed away with DMEM/F-12 (GIBCO) medium. Then, iPS cells, whose diameter is about 10 μm, derived from human fetal lung fibroblasts were adjusted to $5 \times 10^5$ cells/μL in the Essential 8 (GIBCO Inc.) medium to which the ¹/₁₀₀₀ volume of the solution of Rock Inhibitor (Wako Pure Chemical Industries, Ltd.) was added. The iPS cell suspension was added onto the mesh in the same manner as Matrigel and the mesh was incubated in a cell culture device controlled to 37° C. and 5% $CO_2$. The prepared solution for the iPS cells was removed on Day 1 of culture, and the Essential 8 medium was added to the cell culture vessel which was incubated again in the cell culture device. After that, the medium was replaced every 2 days and the cells were observed over time. The results are shown in FIGS. 6(A) and 6(B).

On Day 1 of culture, human iPS cells 14 adhered on the mesh wire 3 of the cell culture substrate. They gradually spread from Day 4 of culture to form a single layer. On Day 12 of culture, it was observed that the iPS cells became cystic and differentiated into blastocysts as shown by arrows. Thus, by using a mesh-shaped cell culture substrate made of a metal and a photocurable resin as a material, iPS cells can be cultured and differentiated into blastocysts without an inducing agent.

Example 2

In this Example, a cell culture substrate with openings of different sizes was prepared and iPS cells were cultured.

Figure 7:
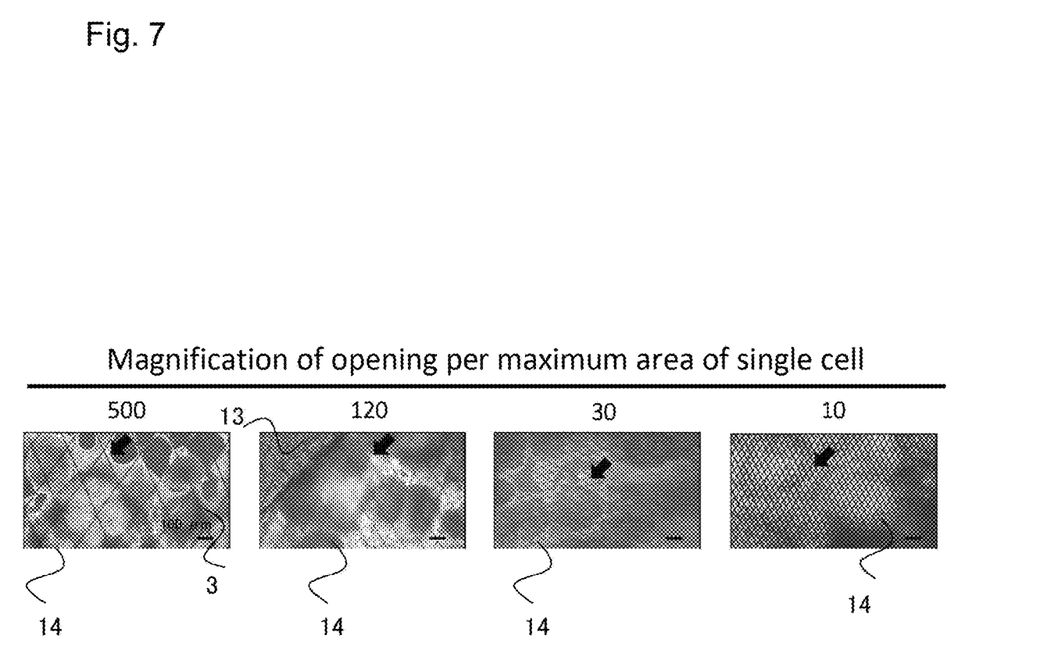
FIG. 7 shows bright-field microscopic images showing results of observation of cell culture on meshes with openings of different areas according to Example 2 of the present invention.

As shown in FIG. 7, nickel meshes with the diamond-shaped openings 2 each having an area of about 10, 30, 120, 500 times the maximum area of the cell and wires of 5 μm diameter were used as a cell culture substrate. The substrates were produced and prepared in the same way as described in Example 1.

Laminin (Sigma Aldrich, 50 μg/mL) adjusted to a concentration of 1 mg/mL was added over the mesh as a scaffold material and treated at 4° C. for 10 days. Subsequently, the scaffold material was removed, and excessive scaffold material was washed away with PBS (pH 7.4). Then, iPS cells derived from human fetal lung fibroblasts were adjusted in the mTeSR (VERITAS Corporation) medium to $5\times10^5$ cells/μL, to which the solution of Rock Inhibitor was added. The human iPS cell suspension was added onto the mesh in the same manner as Laminin and the mesh was incubated in a cell culture device controlled to 37° C. and 5% $CO_2$. The medium was removed on Day 1 of culture, and mTeSR was added and incubated again in the cell culture device. Thereafter, the medium was replaced every 2 days and the cells were observed. The results on Day 13 of culture are shown in FIG. 7.

On Day 1 of culture, the human iPS cells 14 adhered on the mesh wires of the cell culture substrate like the case described in Example 1. On Day 13 of culture, it was observed that the iPS cells became cystic and differentiated into blastocysts as shown by arrows in FIG. 7. Thus, even using the mesh-shaped substrate with the openings each having an area 10 to 500 times larger than the maximum area of the cell, human iPS cells can be cultured and differentiated into blastocysts without an inducing agent.

Example 3

In this Example, iPS cells were cultured using a planar mesh with non-diamond-shaped openings (e.g., a triangle or a circle).

Figure 8A:
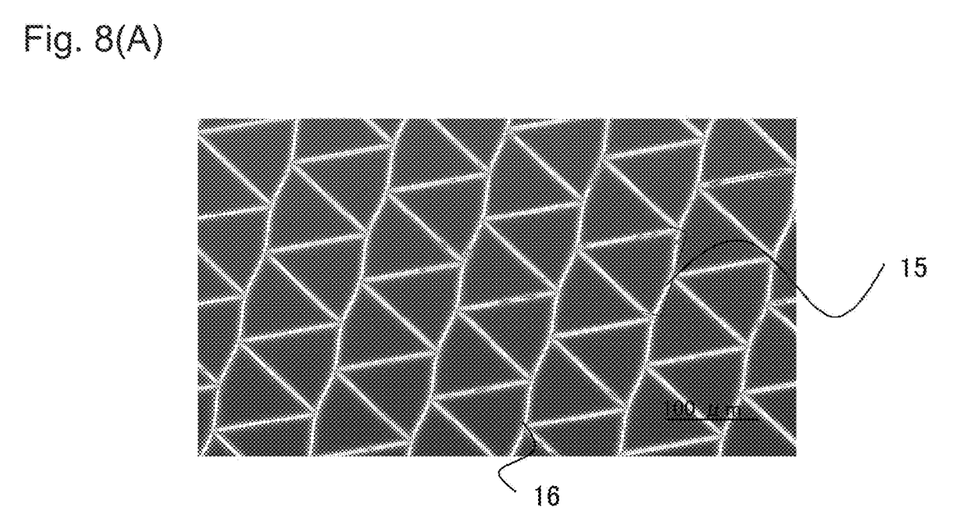
FIGS. 8(A) and 8(B) show microscopic images showing meshes with openings having a shape of an equilateral triangle and a circle, respectively, according to an embodiment of the present invention.
Figure 8B:
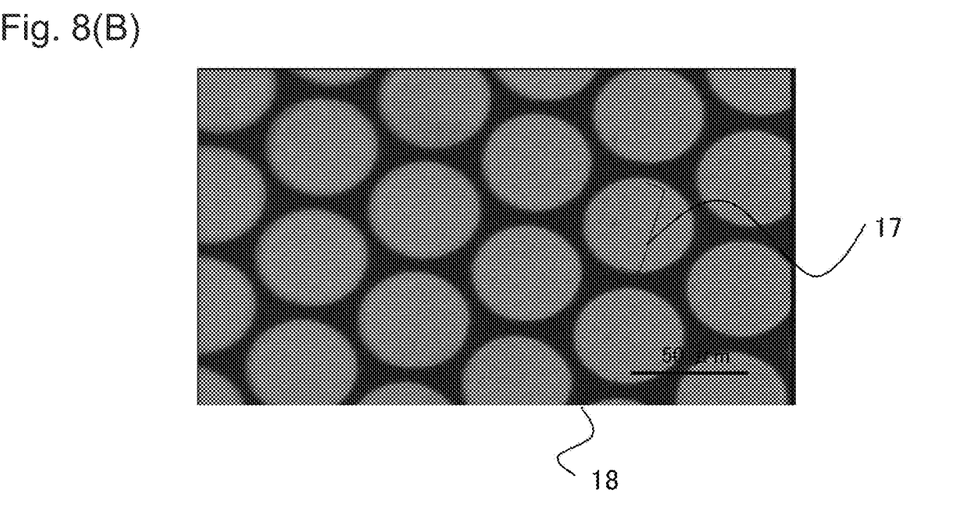

As shown in FIGS. 8(A) and 8(B), nickel meshes (the diameter of each mesh wire 16: 5 μm) with equilateral triangular openings 15 (100 μm each side) and circular openings 17 (50 μm diameter), respectively, (thickness of the mesh 18: 7 μm) were used as cell culture substrates. The nickel meshes were made by electroforming like the case described in Example 1. For each substrate, the produced mesh was reinforced along the periphery thereof with a Kapton tape having a thickness of 100 μm to facilitate handling. The cell culture substrate thus produced was irradiated with a UV lamp for sterilization for 24 hours or more. The sterilized cell culture substrate was placed in the cell culture vessel 5 using the configuration shown in FIG. 2A.

Figure 9A:
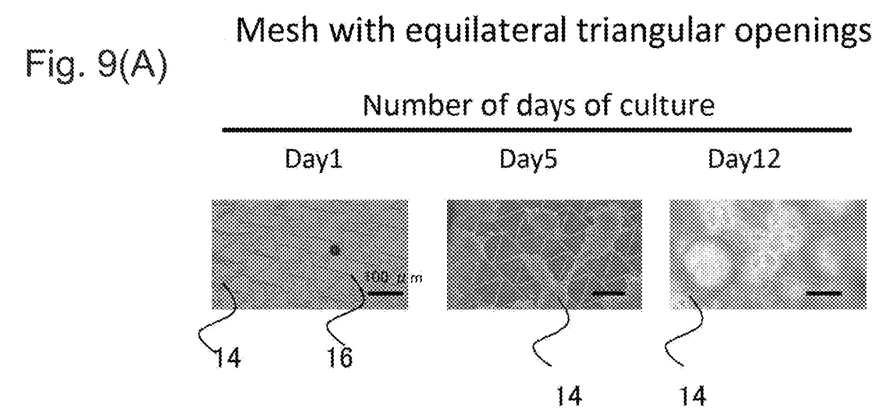
FIGS. 9(A) and 9(B) show bright-field microscopic images showing results of observation of cell culture on meshes with openings having a shape of an equilateral triangle and a circle, respectively, according to Example 3 of the present invention.
Figure 9B:
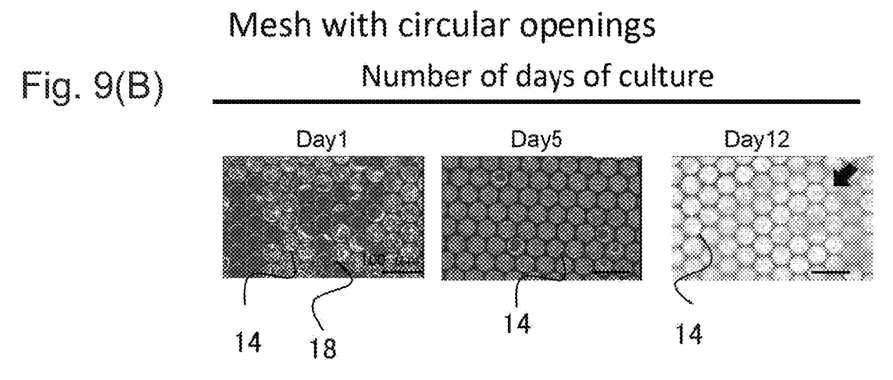

Matrigel (CORNING) adjusted to a concentration of 1 mg/mL was added over the mesh as a scaffold material and treated at 4° C. for 10 days. Subsequently, the Matrigel was removed and the Matrigel left in places other than the mesh was washed away with DMEM/F-12 (GIBCO) medium. Then, iPS cells, whose diameter is about 10 μm, derived from human fetal lung fibroblasts were adjusted to $5\times10^5$ cells/μL in the Essential 8 (GIBCO Inc.) medium, to which 1/1000 volume of the solution of Rock Inhibitor (Wako Pure Chemical Industries, Ltd.) was added. The iPS cell suspension was added onto the mesh in the same manner as Matrigel and the mesh was incubated in a cell culture device controlled to 37° C. and 5% $CO_2$. The medium was removed on Day 1 of culture, and the Essential 8 medium was added to the cell culture vessel so that the cell culture substrate was filled, which was incubated again in the cell culture device. Thereafter, the medium was replaced every 2 days to observe the cells. The results of observation over time are shown in FIGS. 9(A) and 9(B).

On Day 1 of culture, the human iPS cells 14 adhered on the meshes 16 and 18 of the cell culture substrate. Cells gradually spread from Day 5 of culture to form a single layer. On Day 12 of culture, it was observed that iPS cells became cystic and differentiated into blastocysts as shown by an arrow. In this way, by using a mesh-shaped cell culture substrate with the equilateral triangular openings or the circular openings, iPS cells can be cultured and differentiated into blastocysts without an inducing agent.

Example 4

Figure 5:
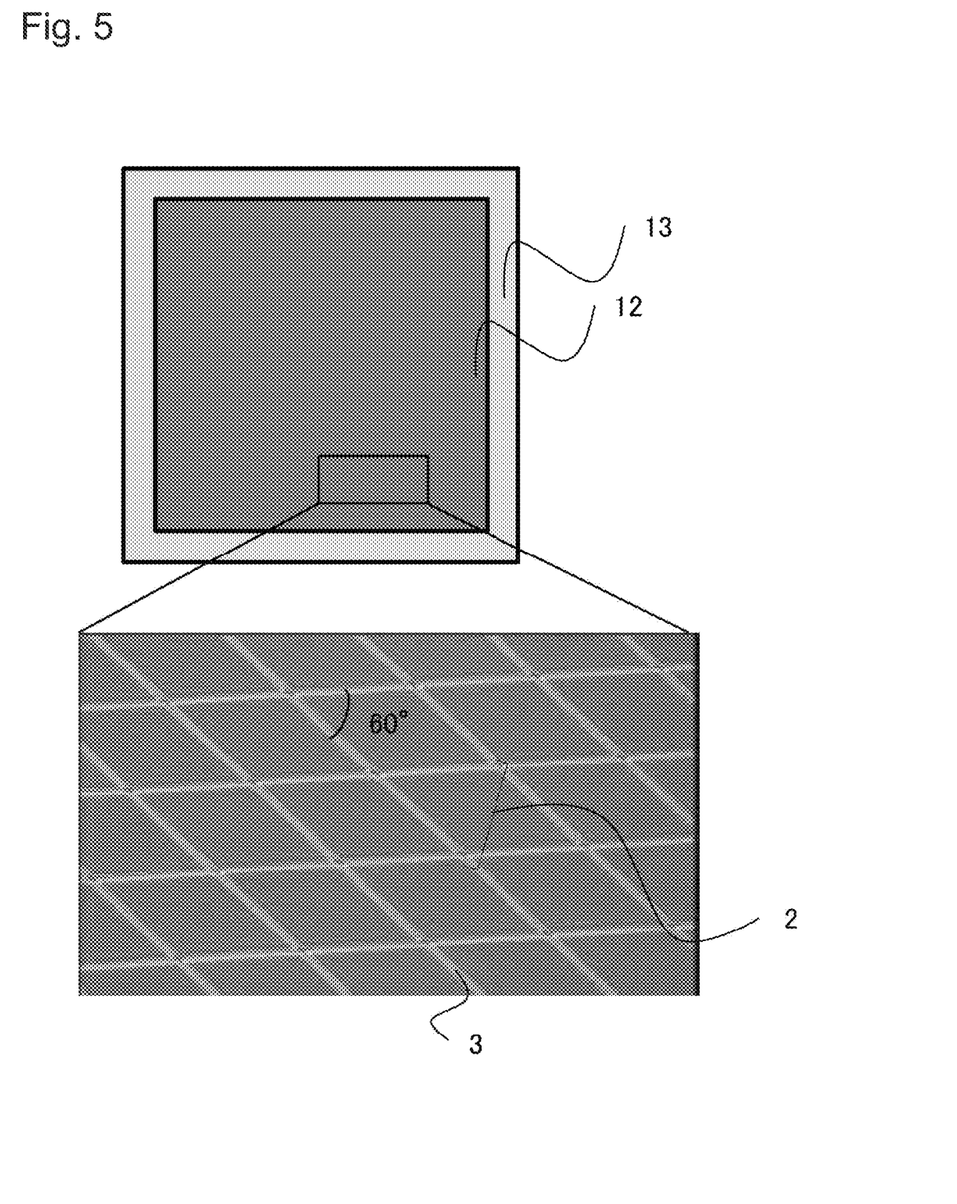
FIG. 5 shows a microscopic image of a mesh with diamond-shaped openings in Example of the present invention.

In this Example, iPS cells were cultured after coating a planar mesh with the polymer. It is shown that the undifferentiated state of iPS cells can be maintained by coating the mesh (mesh wires 3, thickness of 2 to 5 μm) with the diamond-shaped openings 2 each having a minor axis of 200 μm shown in FIG. 5 with a polymer before coating it with a scaffold material.

Nickel or SU-8 was used as a material of the mesh with the diamond-shaped openings. The nickel meshes and SU-8 meshes with the diamond-shaped openings were produced as described in Example 1 and reinforced along the periphery thereof with a Kapton tape 13 having a thickness of 100 μm to facilitate handling.

Next, the mesh was coated with Parylene C (Parylene Japan) having the following chemical formula for preparation of the substrate to have a thickness of about 0.2 to 0.5 μm of the coating. A Labcoater PDS 2010 (Parylene Japan) was used for Parylene C coating, following instruction manuals for reagents and equipment.

[Chemical structure 1]

Figure 10A:
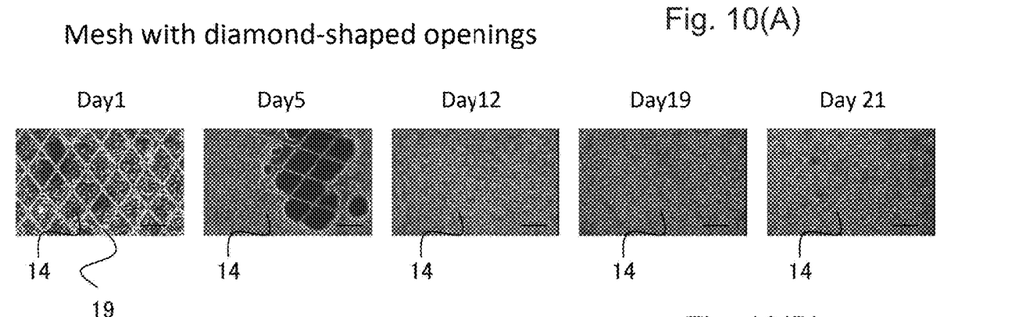
FIGS. 10(A) and 10(B) show bright-field microscopic images showing results of observation of cell culture on meshes coated with Parylene, with diamond-shaped openings and a circle, respectively, according to Example 4 of the present invention.

Next, the cell culture substrate coated with Parylene C was irradiated with a UV lamp for 24 hours or more for sterilization. Subsequently, Matrigel or Laminin adjusted to a concentration of 1 mg/mL was added over the mesh as a scaffold material and treated at 4° C. for 10 days. Subsequently, the scaffold material was removed, and excessive scaffold material was washed away with DMEM/F-12 or PBS (pH 7.4). Then, iPS cells, whose diameter is about 10 μm, derived from human fetal lung fibroblasts were adjusted to $5 \times 10^5$ cells/μL in the Essential 8, to which the solution of Rock Inhibitor was added. The iPS cell suspension was added onto the mesh in the same manner as Matrigel and Laminin and the mesh was incubated in a cell culture device controlled to 37° C. and 5% $CO_2$. The prepared solution for the iPS cells was removed on Day 1 after being incubated, and the Essential 8 medium was added to the cell culture vessel which was incubated again in the cell culture device. After that, the medium was replaced every 2 days and the cells were observed over time. The results are shown in FIGS. 10(A) and 10(B).

On Day 1 of culture, the iPS cells 14 had adhered to the cell culture substrate 19. They gradually spread to form a single layer by Day 5-12 of culture. As shown in Example 1, differentiation into cystic blastocysts was confirmed on Day 12 on the mesh without the Parylene C coating, whereas no differentiation of iPS cells into blastocyst was confirmed on the mesh coated with Parylene C. This result can be confirmed with mesh using nickel as a material.

Figure 10B:
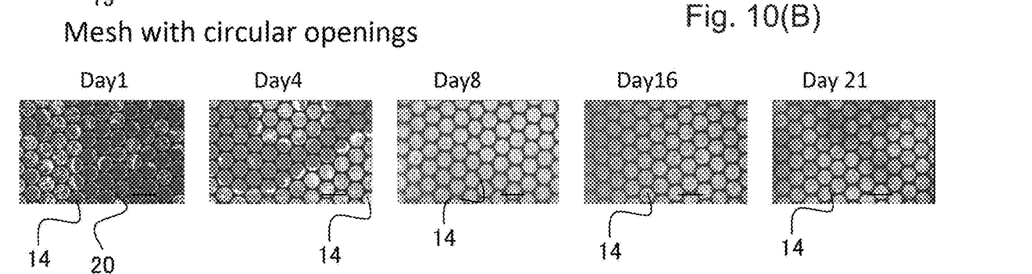

In addition, when a circular mesh made in Example 3 was coated with Parylene C and subjected to the similar experiments, differentiation into cystic blastocysts did not occur as shown in FIG. 10B, as with the mesh with the diamond-shaped openings.

Furthermore, since the iPS cells used in the Examples 1 to 4 secrete human chorionic gonadotropin (hCG) hormone (hereinafter referred to as hCG) when differentiated into blastocysts, the amount of hCG in the culture solution in FIG. 10A was measured on different culture days (on Days 10, 13, 16, and 20). As a control, a culture medium obtained by culturing cells using the cell culture substrate in Example 1 coated with Matrigel without Parylene C coating was used. For quantification, values of OD 450 were measured with an absorbance plate reader (TECAN infinite F50, TECAN) using an hCG ELISA kit (IMMUNOSPEC) based on ELISA reaction. Details of the ELISA reaction and measurement method were in accordance with an instruction manual of the kit.

Figure 11:
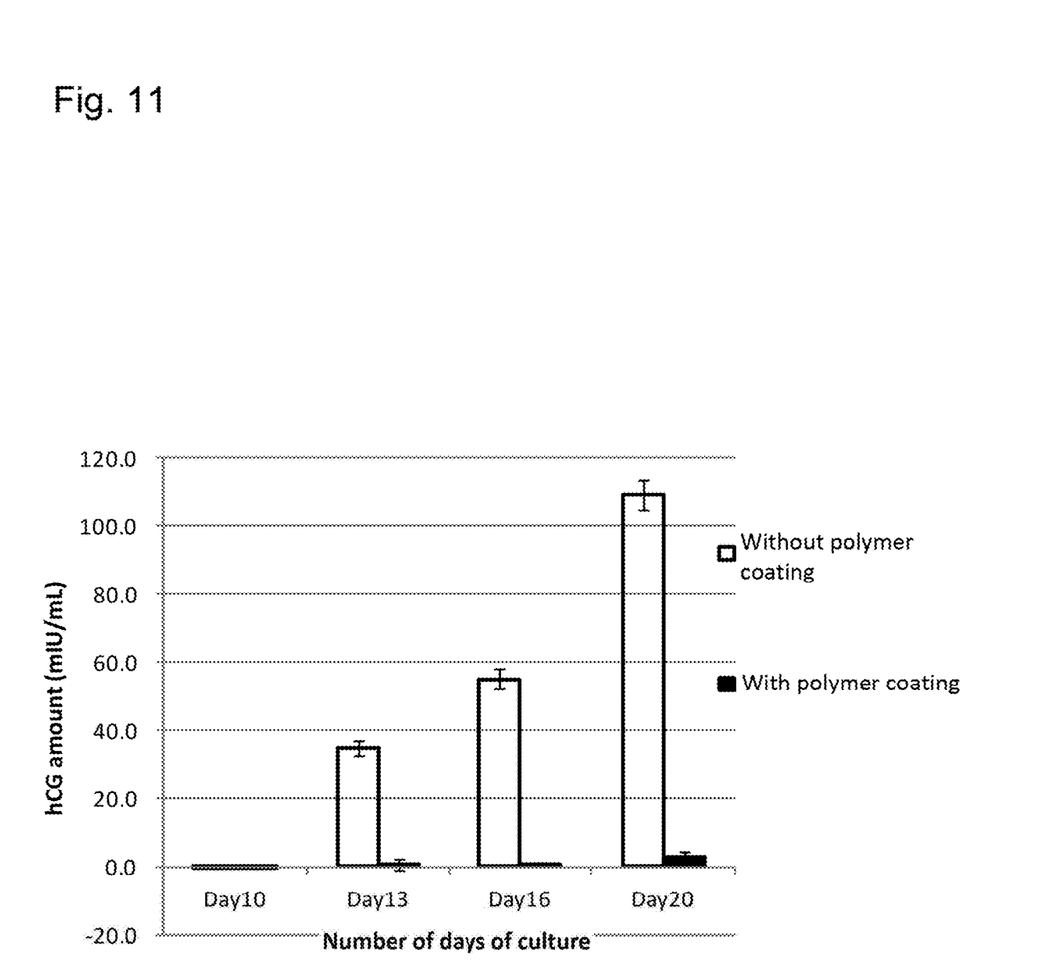
FIG. 11 is a graph showing amounts of hCG hormone in culture mediums used in combination with meshes with diamond-shaped openings with or without Parylene coating in Examples 4 and 1 of the present invention, respectively.

As a result, the amount of hCG in the control culture solution increased after Day 13 of culture. In contrast, when the substrate coated with Parylene C was used, hCG was not detected even after Day 13 of culture, and slightly detected on Day 20 of culture but only about 1/50 of the value obtained in the control (FIG. 11). Similar results were obtained for meshes made of nickel as a material.

As described above, by using the cell culture substrate coated with Parylene C before coated with a scaffold material, the undifferentiated state is maintained even when iPS cells are cultured for a long period of time. Therefore, the use of a cell culture substrate coated with Parylene C before coated with a scaffold material makes it possible to culture iPS cells and maintain them in an undifferentiated state for a long time.

The invention claimed is:

1. A substrate for maintaining an undifferentiation state of a stem cell when used in culture thereof, the substrate having a planar mesh structure and being coated with a polymer,
   wherein the polymer is a xylene resin and the undifferentiated state of the stem cell is maintained for at least 12 days,
   wherein the substrate comprises a metal and wherein the metal is nickel, and
   wherein the planar mesh structure is made of wire-like substrates, each wire-like substrate having a maximum diameter of 10 μm and each opening of the mesh having a minimum width of 30 μm.

2. The substrate of claim 1, wherein each opening of the mesh has an area being equal to or larger than an area of the stem cell to be cultured.

3. The substrate of claim 1, wherein each opening has an area of 100 $μm^2$ or larger.

4. The substrate of claim 1, wherein the stem cell is a pluripotent stem cell.

5. The substrate of claim 1, wherein
the xylene resin is a p-xylene polymer.

6. The substrate of claim 1, wherein
the substrate is coated with a scaffold material after being coated with the xylene resin.

7. A cell culture vessel comprising:
a holding mechanism for holding the substrate of claim 1 in a state of being suspended in a culture medium.

8. The cell culture vessel of claim 7, comprising a plurality of holding mechanisms.

9. A method for cell culture comprising the steps of:
seeding a cell onto the substrate of claim 1; and
culturing the cell with the substrate held in a state of being suspended in a culture medium.

10. The method of claim 9, wherein
the cell is cultured with a plurality of substrates stacked in a single cell culture vessel.

* * * * *